US012779006B2

(12) United States Patent
Banerjee et al.

(10) Patent No.: US 12,779,006 B2
(45) Date of Patent: Nov. 3, 2026

(54) NUTRACEUTICAL COMPOSITION AND METHOD OF PRODUCTION THEREOF

(71) Applicant: Indian Institute of Technology Bombay, Mumbai (IN)

(72) Inventors: Rinti Banerjee, Mumbai (IN); Swati V. Pund, Mumbai (IN); Roshan Keshari, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 987 days.

(21) Appl. No.: 17/923,618

(22) PCT Filed: May 5, 2021

(86) PCT No.: PCT/IN2021/050436

§ 371 (c)(1),
(2) Date: Nov. 7, 2022

(87) PCT Pub. No.: WO2021/224943

PCT Pub. Date: Nov. 7, 2021

(65) Prior Publication Data

US 2023/0104634 A1 Apr. 6, 2023

(30) Foreign Application Priority Data

May 5, 2020 (IN) ............................ 202021019129

(51) Int. Cl.

| | |
|---|---|
| ***A61K 36/61*** | (2006.01) |
| ***A61K 9/127*** | (2006.01) |
| ***A61K 31/085*** | (2006.01) |
| ***A61K 31/4525*** | (2006.01) |
| ***A61K 36/67*** | (2006.01) |
| ***A61K 47/22*** | (2006.01) |
| ***A61K 47/24*** | (2006.01) |
| ***A61P 31/00*** | (2006.01) |

(52) U.S. Cl.

CPC .............. *A61K 36/61* (2013.01); *A61K 9/127* (2013.01); *A61K 31/085* (2013.01); *A61K 31/4525* (2013.01); *A61K 36/67* (2013.01); *A61K 47/22* (2013.01); *A61K 47/24* (2013.01); *A61P 31/00* (2018.01)

(58) Field of Classification Search

None

See application file for complete search history.

(56) References Cited

U.S. PATENT DOCUMENTS

| | | | | |
|---|---|---|---|---|
| 5,650,172 A * | 7/1997 | Matsuda | .................. | A61K 9/19<br>514/561 |
| 2016/0338923 A1* | 11/2016 | Grune | ...................... | A61K 8/27 |

FOREIGN PATENT DOCUMENTS

| | | | |
|---|---|---|---|
| WO | WO-2018099570 A1 * | 6/2018 | ............. A61Q 19/10 |

* cited by examiner

*Primary Examiner* — Nannette Holloman
(74) *Attorney, Agent, or Firm* — Rivka Friedman

(57) ABSTRACT

The present invention provides nutraceutical composition comprising essential bioactives such as spice powders and their extracts in a vesicle made up of edible amphiphilic lipid as emulsifiers and surfactants for antioxidant, antiviral, antibacterial, antifungal and anti-inflammatory effects. Specifically, the nutraceutical composition of the present invention synergistically enhances intestinal absorption and helps in reducing inflammation and infections. The present invention also provides a method of producing the afore-mentioned nutraceutical composition.

11 Claims, 5 Drawing Sheets

| Pathogen | Percentage reduction |
|---|---|
| *Escherichia coli* [MTCC-1687] | 99.999 % |
| *Staphylococcus aureus* [MTCC-737] | 99.999 % |
| *Candida abicans* [MTCC-183] | 99.999 % |
| *Aspergillus niger* [MTCC-9933] | 99.999 % |
| *Escherichia coli: phage MS2* (ATCC 15597 B1) | 99.999 % |

| *Minimum bacteriocidal concentration (mg/ml)* | |
|---|---|
| | *MR-S.aureus* |
| *Clove* | *9.4* |
| *Specific composition of Nutraceutical* | *4.7* |

| | Percent mortality (up to Day 14) | |
|---|---|---|
| Dose (mg/Kg) | Rat | Mice |
| 300mg | 0 | 0 |
| 2000mg | 0 | 0 |

NUTRACEUTICAL COMPOSITION AND METHOD OF PRODUCTION THEREOF

FIELD OF THE INVENTION

The present invention relates to field of nutraceutical and more particularly to nutraceutical composition comprising encapsulated forms of essential bioactives such as spice powders and their extracts in a vesicle made up of edible amphiphilic lipid as emulsifiers and surfactants for antioxidant, antiviral, antibacterial, antifungal and anti-inflammatory effects. Specifically, the nutraceutical composition of the present invention helps in reducing risk of respiratory inflammation and infections. The present invention also relates a method of producing the afore-mentioned nutraceutical composition.

BACKGROUND OF THE INVENTION

Anti-inflammatory and anti-infective properties with high absorption of bioactives is required for preventing the risk of many inflammatory and infectious diseases. For example, persistent inhalation of the invading pathogens or toxic agents may result in overwhelming production of ROS. An intense inflammatory response in the lungs is responsible for acute lung injury/ARDS with accumulation of both pro- and anti-inflammatory cytokines in bronchoalveolar lavage (BAL) fluid. Oxidative stress is a deleterious process that leads to lung damage and consequently to various disease states. Oxidants initiate a number of pathologic processes, including inflammation of the airways, which may contribute to the pathogenesis and/or exacerbation of airways disease. During inflammation, enhanced ROS production may induce recurring DNA damage, inhibition of apoptosis, and activation of protooncogenes by initiating signal transduction pathways. Therefore, it is conceivable that chronic inflammation-induced production of ROS in the lung may predispose individuals to lung diseases. By decreasing the ROS levels actively, focusing on antioxidant levels, and blocking the inflammatory response-related signaling pathways, dietary pattern management can help in preventing the disease progression.

There are no potent effective nutraceutical combinations with high absorption which reduce pulmonary inflammation associated with lung injury and infections.

Chinese patent application no. CN1875960A describes nanoemulsion medicine of eugenol and preparation method thereof. The product comprising isopropyl myristate, croton oil, vitamin E oil, tween-80, spans-80 and eugenol 0.1-10%, for improving antibiosis, anti-inflammation, disinfection, analgesic, and antiparasitic.

EP2555763A1 describes viral inhibitor compositions for in vivo therapeutic use comprising combination of (-) -carvone, geraniol and a further essential oil component. The product compositions containing essential oil components for treatment and prevention of diseases caused by DNA enveloped/non-enveloped, RNA enveloped/non-enveloped viruses. Orally, topically, by inhalation, by suppository, IV, SC, IM. Type and nature of formulations are not addressed.

U.S. Pat. No. 9,439,416B2 describes compositions and methods comprising terpenes or terpene mixture selected from thymol, eugenol, geraniol, thymol, citral and L-carvone, suitable for treating plant infections.

Eugenol based nutraceutical for preventing or treating atopic dermatitis is described in WO2015060677A as a pharmaceutical, nutraceutical, functional health food, a quasi-drug, and a cosmetic composition.

None of the compositions mentioned in the above patent applications pertains to a soluble, stable, encapsulated forms of bioactives such as spice powders including clove, with or without black pepper along with phospholipids and surfactants exhibiting significant antioxidant antiviral, antibacterial, antifungal and anti-inflammatory effects and other bioactivities, in a ready to use form and a composition for beverage and food applications to deliver physiologically relevant amounts of phytonutrients per serving without any taste or aroma issue and in organic quality.

SUMMARY OF THE INVENTION

In one aspect, the present invention provides a nutraceutical composition comprising: a bioactive encapsulated in a vesicle;

wherein the vesicle consists of an amphiphilic emulsifier & an antioxidant surfactant;

wherein the bioactive is clove powder and/or extracts thereof; and wherein the proportion of bioactive to vesicle is present in the ratio from 4:1 to 1:1.

In another aspect, the present invention provides a method of producing the afore-mentioned nutraceutical composition comprising:

a) dissolving 400 to 500 mg of lecithin in water and heating at 55° C. for 45 minutes to 90 minutes;
b) adding 50 to 100 mg of oleic acid and 20 to 50 mg of tocopherol esters to lecithin solution of step (a) and heated to form smooth milky suspension;
c) adding superfine pulverized 1 to 2 g of a bioactive clove powder to the suspension of step (b);
d) homogenizing the mixture of step (c) at 12000 rpm for 15 minutes to 30 minutes to form the vesicle encapsulating the bioactive.

In yet another aspect, the present invention provides the afore-mentioned nutraceutical composition for use in drinks, beverages, syrups, dietary supplements, food and animal feed.

In a further aspect, the present invention provides the afore-mentioned nutraceutical composition for use in the treatment and prevention of inflammations and infections related to acute lung injury, acute respiratory distress syndrome (ARDS) and severe acute respiratory syndrome (SARS).

BRIEF DESCRIPTION OF THE DRAWINGS

The foregoing summary, as well as the following detailed description of the invention will be better understood when read in conjunction with the appended drawings. For the purpose of assisting in the explanation of the invention, there are shown in the drawings embodiments which are presently preferred and considered illustrative. It should be understood, however, that the invention is not limited to the precise arrangements and instrumentation shown therein.

FIG. 5(*a*) shows reduction in transepithelial electrical resistance of CaCo-2 cells with time post treatment with nutraceutical formulation and FIG. 5(*b*) shows enhanced permeability of hydrophobic molecule, FITC across Caco2 monolayer. It indicates that nutraceutical formulation has ability to enhance the intestinal absorption.

FIG. 6(*a*) shows changes in body weight for 14 days after administration of 2000 mg per Kg of formulation in rat and mice. FIG. 6(*b*) shows no morbidity observed till 14 days after administration of 300 mg per kg and 2000 mg per kg dose in rat and mice. It confirms the safety of formulation in two species rats and mice.

DESCRIPTION OF THE INVENTION

Figures 1, 2:
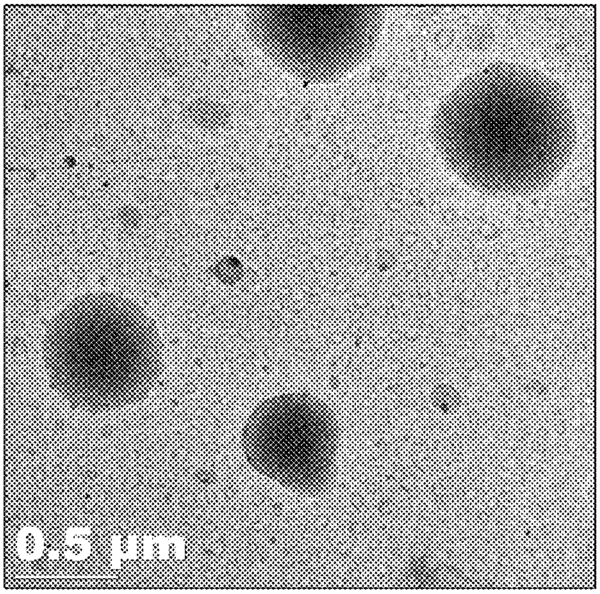
FIG. 1: Transmission electron microscopy (TEM) image of nutraceutical lipid vesicles showing spherical particles.
FIG. 2: Antimicrobial properties of the nutraceutical showing percentage reduction in bacterial, fungal and viral load post treatment with nutraceutical. It confirms the broad-spectrum antimicrobial effect of formulation.

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification are to be understood as being modified in all instances by the term "about". It is noted that, unless otherwise stated, all percentages given in this specification and appended claims refer to percentages by weight of the total composition.

Thus, before describing the present invention in detail, it is to be understood that this invention is not limited to particularly exemplified process parameters that may of course, vary. It is also to be understood that the terminology used herein is for the purpose of describing particular embodiments of the invention only, and is not intended to limit the scope of the invention in any manner.

The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

It must be noted that, as used in this specification and the appended claims, the singular forms "a," "an" and "the" include plural referents unless the content clearly dictates otherwise.

The terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As used herein, the terms "comprising" "including," "having," "containing," "involving," and the like are to be understood to be open-ended, i.e., to mean including but not limited to.

As used herein, the term "bioactive agent" refers to any entity (including but not limited to the active ingredient) that has, is intervening or participates in biological activity. In various embodiments, the bioactive agent may be spice powder selected from but not limited to clove pepper powder and black pepper powder. The bioactive agent may also include extracts of spice powders such eugenol (clove powder) or piperine (from black pepper powder).

As used herein, the term "vesicle" and its synonym "liposome" are used herein to identify a generally spherical liquid structure of amphiphilic compounds such as phospholipids. Vesicles/liposomes can be of various sizes and formed as a monolayer (unilamellar) or multilayer (multilamellar) structure. Thus, there are several types of vesicles or liposomes that are all within the scope of the present invention: MLU (multilayer vesicle), SUV (small monolayer vesicle) and LUV (large monolayer vesicle) or GUV (giant single membrane vesicles). The composition of the present invention may also be developed in the form of encapsulated emulsions using amphiphilic compounds In one aspect, the present invention provides a nutraceutical composition comprising encapsulated forms of essential bioactives such as spice powders and their extracts; bioactives in the form of essential oils and their phenols in a vesicle made up of edible amphiphilic lipid as emulsifiers and surfactants for antioxidant, antiviral, antibacterial, antifungal and anti-inflammatory effects. Specifically, the nutraceutical composition of the present invention helps in reducing risk of respiratory inflammation and infections.

The nutraceutical composition of the present invention comprises lipid based amphiphilic emulsifier and antioxidant surfactant which encapsulates one or more of essential bioactive such as spice powder and/or extracts thereof.

Accordingly, the present invention provides a nutraceutical composition comprising: a bioactive encapsulated in a vesicle;

wherein the vesicle consists of an amphiphilic emulsifier & an antioxidant surfactant;

wherein the bioactive is clove powder and/or extracts thereof; and wherein the proportion of bioactive to vesicle is present in the ratio from 4:1 to 1:1.

In an embodiment of the present invention, the amphiphilic emulsifier is a lipid made up of lecithin alone or a combination of lecithin with oleic acid or other edible oils.

In an embodiment of the present invention, said antioxidant surfactant may be a tocopherol ester selected from tocopherol acetate and tocopherol polyethylene glycol succinate.

In an embodiment, the present invention comprises of synergistic combinations of clove powder, optionally pepper powder in a vesicle made up of lecithin, high oleic acid oils and tocopherol polyethylene glycol succinate. The lecithin, oleic acid and tocopherol ester is present in the ratio of 9:1:0.5 to 10:2:1.5.

In an embodiment of the present invention, the vesicle is present in the size range of 300 nm to 20 μm (microns).

Clove powder has strong antiviral properties and also has anti-inflammatory or immunomodulatory effects. Black Pepper powder acts synergistically to enhance absorption.

Lecithin and oleic acid/high oleic acid oils act as permeation enhancers and helps in uptake of bioactives (i.e. spice powder and/or their extracts) which are poorly soluble.

Tocopherol polyethylene glycol succinate acts as an antioxidant and stabilizing agent.

In an embodiment of the invention, the nutraceutical composition consists of at least one spice powder particularly clove powder and/or its extract and stabilized using amphiphilic emulsifiers. The nutraceutical composition is made by forming nanovesicles using lipid hydration and high speed homogenization method which encapsulates the clove powder and/or its extract.

In an embodiment of the present invention, the spice powder is clove powder and extracts thereof. The bioactive may further comprise black pepper powder and/or extracts thereof. The extract of clove powder is eugenol whereas the extract of black pepper powder may be piperine.

In an embodiment of the present invention, the bioactive may further comprise eugenol or piperine. Eugenol from clove oil is present in the range of 0.1% to 6%, piperine from pepper is present in the range of 0 to 1.5%, of total weight of composition.

The clove powder is present in the range of 10% to 50% of total weight of composition and black pepper powder in the range of 0-15%.

FIG. 1 depicts the TEM image of clove extract nutraceutical product. Uniform vesicles are formed.

Figure 7:
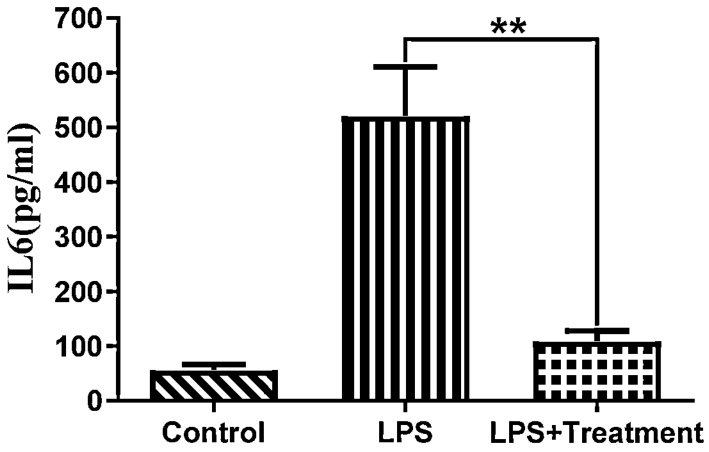
FIG. 7: Effect of nutraceutical on cytokine storm. Increased IL 6 in bronchioalveolar fluid of rat after LPS mediated injury, which was reduced on treatment with nutraceutical formulation. This shows anti-inflammatory potential of nutraceutical formulation.

In vitro antimicrobial activity shows 99.99% reduction in bacteria, fungal and viral loads (FIG. 2). The nutraceutical composition also showed in vitro viral and RNA degradation as well as reduced the viral replication. (FIG. 4) In vivo toxicity revealed the safety of composition. In vivo anti-inflammatory activity is tested in endotoxin induced lung inflammation in rats. Significant reduction in levels of IL-6 in bronchoalveolar lavage fluid is seen in the treated group (FIG. 7).

In an embodiment of the present invention, the nutraceutical composition is optionally lyophilized using sugar alcohol based cryoprotectant selected from cyclodextrins and mannitol.

In an embodiment of the present invention, the nutraceutical composition is further provided in one form selected from the group of a liquid, a powder, a capsule, and a tablet.

In another aspect, the present invention provides a method of producing the afore-mentioned nutraceutical composition comprising:

a) dissolving 400 to 500 mg of lecithin in water and heating at 55° C. for 45 minutes to 90 minutes;

b) adding 50 to 100 mg of oleic acid and 20 to 50 mg of tocopherol esters to lecithin solution of step (a) and heated to form smooth milky suspension;

c) adding superfine pulverized 1 to 2 g of a bioactive clove powder optionally with 5 to 20 mg of black pepper powder to the suspension of step (b);

d) homogenizing the mixture of step (c) at 12000 rpm for 15 minutes to 30 minutes to form the vesicle encapsulating the bioactive.

In an embodiment of the present invention, the proportion of spice powder to lipid range from 4:1 to 1:1.

In an embodiment of the present invention, superfine pulverized 5 to 20 mg of black pepper powder is optionally added with clove powder to the suspension of step (b).

In an embodiment of the present invention, eugenol and/or piperine is optionally added to the vesicles of step (d) in the ratio of 100:1 to 50:1.

In an alternate embodiment of the invention, the invented nutraceutical formulation is prepared by high speed homogenization of edible lecithin mixed with oleic acid (9:1) in water containing tocoferol derivatives at 12000 rpm for 15-30 min at 55° C. Eugenol alone or along with piperine is added slowly to the nanovesicles and carefully mixed with lipid to eugenol ratio 10:6 to 10:2.

In another aspect, the nutraceutical composition of the present invention may be used in liquid form, as drinks, beverages, syrups, dietary supplements, and presented as solid form like food, animal feed.

In yet another aspect, the present invention also provide a multifunctional, anti-inflammatory, antibacterial and antiviral nutraceutical composition for use in the treating, preventing, or alleviating inflammations and infections such as but not limited to acute respiratory distress syndrome (ARDS), acute lung injury and severe acute respiratory syndrome (SARS). The said nutraceutical composition may also be used for infection associated with lung injury. The said nutraceutical composition may also be used for reducing the oxidative stress and inflammation in the respiratory tract.

The following examples are provided to better illustrate the present invention and are not to be interpreted in any way as limiting the scope of the invention. All specific materials and methods described below, in whole or in part, fall within the scope of the invention. These specific compositions, materials, and methods are not intended to limit the invention, but merely to illustrate specific embodiments falling within the scope of the invention. One skilled in the art may develop equivalent materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

EXAMPLES

Example 1

The invented nutraceutical composition is made by following high speed homogenization method. 400 to 500 mg of lecithin is dissolved in warm water and heated at 55° C. for 45 minutes to 90 minutes. 50 to 100 mg oleic acid and 20 to 50 mg tocopherol esters are added to lecithin and heated to make a smooth milky suspension. Then superfine pulverized clove powder (1 to 2 g) is added. The mixture is homogenized on high speed homogenizer at 12000 rpm for 15-30 min. The process spontaneously forms vesicles and yields a homogenous spice suspension.

Example 2

The invented nutraceutical composition is made by following high speed homogenization method. 400 to 500 mg of lecithin is dissolved in warm water and heated at 55° C. for 45 minutes to 90 minutes. 50 to 100 mg oleic acid and 20 to 50 mg tocopherol esters are added to lecithin and heated to make a smooth milky suspension. Then superfine pulverized clove powder (1 to 2 g) and black pepper powder (5 to 20 mg) are added. The mixture is homogenized on high speed homogenizer at 12000 rpm for 15-30 min. The process spontaneously forms vesicles as shows in FIG. 1 and yields a homogenous spice suspension. Clove and pepper powder are commercially procured as off the shelf purchases.

Example 3

The invented nutraceutical composition consisting of vesicles exhibited antimicrobial activity. The composition shows 99.99% inhibition of bacteria, fungal and viral species (FIG. 2). Composition exhibits a strong broad spectrum antimicrobial activity. Composition exhibits better antimicrobial activity as compared to only clove against drug resistant bacteria (FIG. 2, below table).

Figures 3, 4:
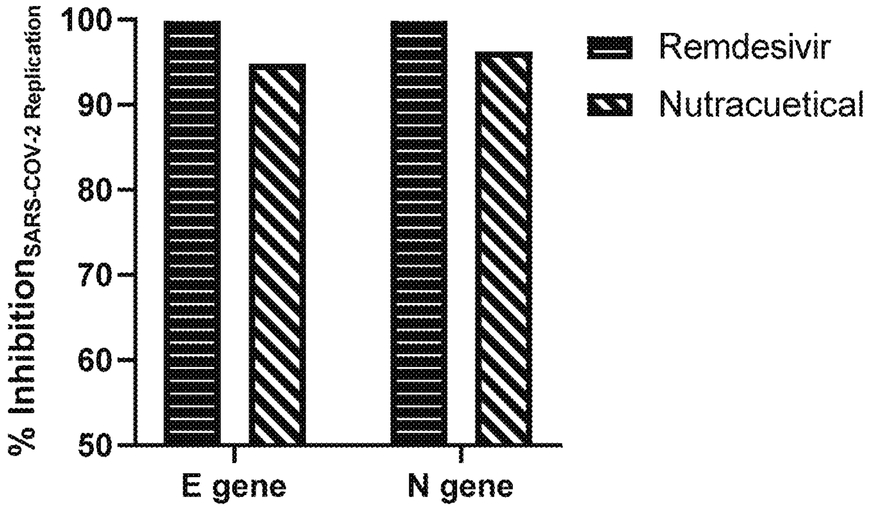
FIG. 3: A table which shows synergism of composition of nutraceutical composition with clove w.r.t to minimum bactericidal concentration on drug resistant bacteria.
FIG. 4: Comparison of Severe acute respiratory syndrome coronavirus 2 (SARS-CoV-2) viral replication inhibition with remdesivir in veroE6 cells after 48-hour treatment. Nutraceutical shows comparable inhibition of SARS-COV-2 replication with remdesivir.

Composition shows inhibition of viral replication inside mammalian cells as compared to remdesivir (FIG. 4).

Example 4

Figure 5A:
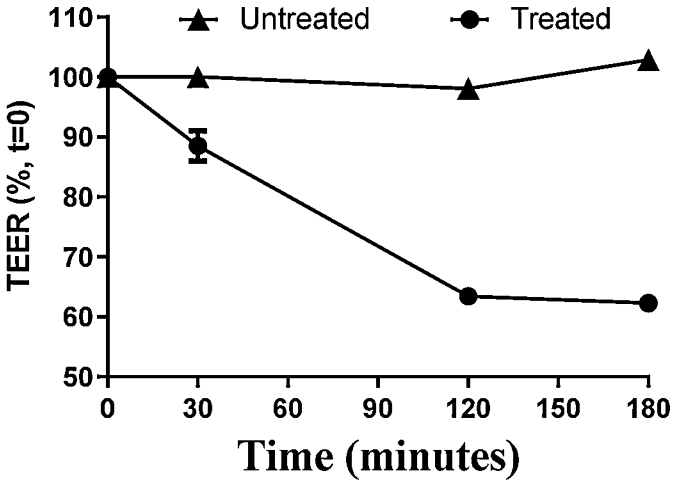
FIG. 5: Effect of nutraceutical formulation on intestinal permeability.
Figure 5B:
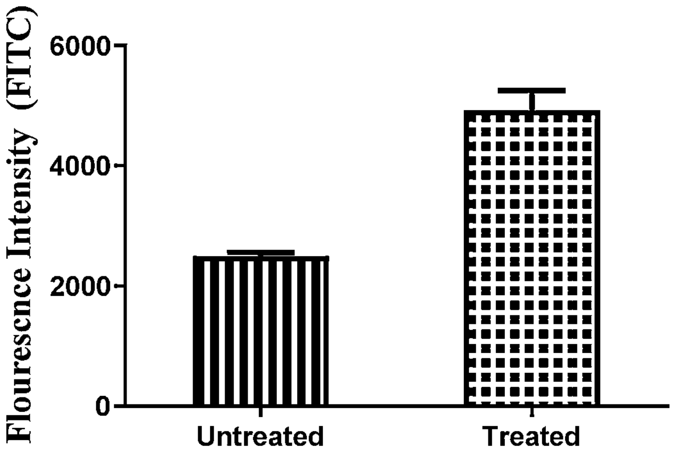

The invented nutraceutical composition shows significant enhancement of absorption through monolayer formed by intestinal cells—CaCo-2 cells. Decrease in trans-epithelial electrical resistance (FIG. 5*a*) and increase in permeation of molecules across barrier (FIG. 5*b*) indicates the enhanced absorption through intestinal wall.

Example 5

Figures 6A, 6B:
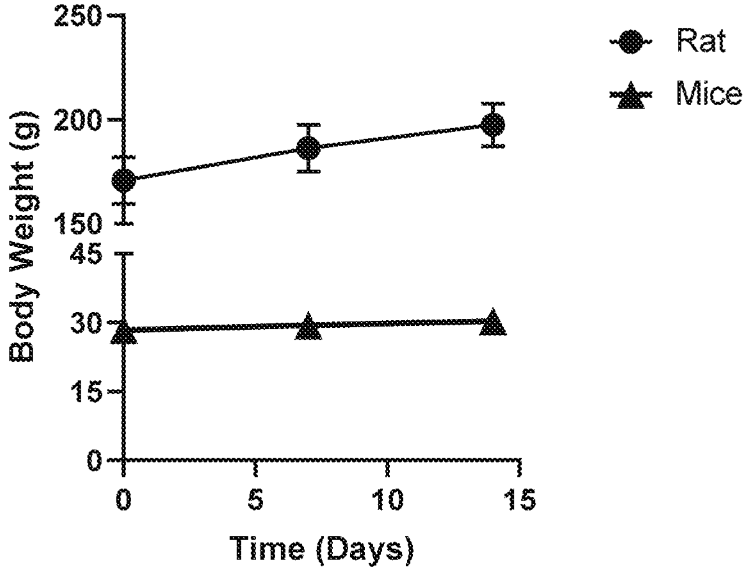
FIG. 6: Effect of high doses of nutraceutical formulation on animal health.

Toxicity was tested on two species. There was no decrease in body weight of two species for 14 days (FIG. 6*a*) and no morbidity was observed in all the tested rats and mice (FIG. 6*b*). Efficacy of nutraceutical composition was tested on LPS injury model in rats. Treatment with nutraceutical reduced the cytokine, IL6 levels in lungs of LPS inflamed model (FIG. 7).

The invention claimed is:

1. A nutraceutical composition comprising:

a bioactive encapsulated in a vesicle;

wherein the vesicle consists of lecithin, oleic acid and tocopherol ester;

wherein the bioactive is clove powder; and wherein the proportion of bioactive to vesicle is present in the ratio from 4:1 to 1:1.

2. The nutraceutical composition as claimed in claim 1, wherein the antioxidant surfactant is tocopherol ester selected from tocopherol acetate and tocopherol polyethylene glycol succinate.

3. The nutraceutical composition as claimed in claim 1, wherein lecithin, oleic acid and tocopherol ester is present in the ratio of 9:1:0.5 to 10:2:1.5.

4. The nutraceutical composition as claimed in claim 1, wherein the bioactive further comprises black pepper powder.

5. The nutraceutical composition as claimed in claim 1, wherein the bioactive further comprises eugenol or piperine.

6. The nutraceutical composition as claimed in claim 1, wherein the vesicle is present in the size range of 300 nm to 20 μm.

7. The nutraceutical composition as claimed in claim 1, wherein the composition is optionally lyophilized using sugar alcohol based cryoprotectant selected from cyclodextrins and mannitol.

8. The nutraceutical composition as claimed in claim 1, further comprising providing the nutraceutical composition in one form selected from the group of a liquid a powder, a capsule, and a tablet.

9. A method of preparing the nutraceutical composition as claimed in claim 1, comprising:

a) dissolving 400 to 500 mg of lecithin in water and heating at 55° C. for 45 minutes to 90 minutes;

b) adding 50 to 100 mg of oleic acid and 20 to 50 mg of tocopherol esters to lecithin solution of step (a) and heated to form smooth milky suspension;

c) adding superfine pulverized 1 to 2 g of a bioactive clove powder to the suspension of step (b); and d) homogenizing the mixture of step (c) at 12000 rpm for 15 minutes to 30 minutes to form the vesicle encapsulating the bioactive.

10. The method as claimed in claim 9, wherein superfine pulverized 5 to 20 mg of black pepper powder is optionally added with clove powder to the suspension of step (b).

11. The method as claimed in claim 9, wherein eugenol or piperine is optionally added to the vesicles of step (d) in the ratio of 100:1 to 50:1.

* * * * *